(12) United States Patent
Palma

(10) Patent No.: US 7,666,858 B2
(45) Date of Patent: Feb. 23, 2010

(54) PHARMACEUTICAL COMPOSITION FOR TREATMENT OF PHIMOSIS USING TOPICAL CORTICOSTEROID

(75) Inventor: Paulo César Rodrigues Palma, Svo Paulo (BR)

(73) Assignee: Apsen Farmaceutica S.A., Sao Paulo (BR)

( * ) Notice: Subject to any disclaimer, the term of this patent is extended or adjusted under 35 U.S.C. 154(b) by 1122 days.

(21) Appl. No.: 10/465,977

(22) PCT Filed: Dec. 13, 2001

(86) PCT No.: PCT/BR01/00154

§ 371 (c)(1),
(2), (4) Date: Oct. 31, 2003

(87) PCT Pub. No.: WO02/053137

PCT Pub. Date: Jul. 11, 2002

(65) Prior Publication Data

US 2004/0067922 A1 Apr. 8, 2004

(30) Foreign Application Priority Data

Dec. 28, 2000 (BR) .................................... 0006556

(51) Int. Cl.
*A61K 31/56* (2006.01)
*A61K 38/46* (2006.01)

(52) U.S. Cl. .................................... 514/171; 424/94.62

(58) Field of Classification Search ................. 514/171; 424/94.62

See application file for complete search history.

(56) References Cited

OTHER PUBLICATIONS

Lamprakopoulos et al. The use of betamethasone and hyaluronidase injections in the treatment of Peyronie's Disease. Scand J Urol Nephrol 34:355-360 (2000).*
Dewan et al. Review Article. Phimosis: is circumcision necessary? Journal of Paediatrics and Child Health, vol. 32, No. 4: 285-289 (1996).*
DeVries et al. Reduction of Paraphimosis with Hyaluronidase. Urology, vol. 48, No. 3 464-465 (1996).*
Adriana Popovici, *Resorption of Hydrocortisone Acetate From Hudrophil Ointments*, Farmacia (Bucharest) 1972, 20(10), 621-32.
A. Lamprakopoulos, *Use of Betamethasone and Hyaluronidase Injections in the Treatment of Peyronie's Disease*, Scandinavian Journal of Urology and Nephrology, Jul. 5, 2000.

* cited by examiner

*Primary Examiner*—Raymond J Henley, III
(74) *Attorney, Agent, or Firm*—Wood, Herron & Evans, L.L.P.

(57) ABSTRACT

This invention addresses the pharmaceutical composition for topical corticosteroid use in association with diffusing enzyme for treatment of phimosis. A pharmaceutical composition for treatment of phimosis using topical corticosteroid characterized by including around 0.025 to 5 percent in weight in relation to the total weight of the mixture composition of one or more corticosteroids and/or hormone steroids, whether or not associated with non-hormonal anti-inflammatory agents and around 25 UTR to 4000 UTR/g of one or more proteolytic diffusing enzymes in proper medium, in different pharmaceutical forms, accompanied with additives known to the technical man. Topical corticosteroid application in association with diffusing enzyme for treatment of phimosis in which 90 percent of the patients had improvements over their clinical complaints, with the prepuce being easily retracted.

8 Claims, No Drawings

PHARMACEUTICAL COMPOSITION FOR TREATMENT OF PHIMOSIS USING TOPICAL CORTICOSTEROID

This application is a national phase application under 35 U.S.C. 371 claiming the benefit of PCT/BR01/00154 (International Publication No. WO 02/053137), which was filed on Dec. 13, 2001, and which has priority based on Brazilian Patent Application PI 0006556-0, filed on Dec. 28, 2000.

This invention addresses the use of pharmaceutical composition for topical corticosteroid and/or hormonal steroids in association with proteolytic diffusing enzyme, whether or not in the presence of non-hormonal anti-inflammatory agents, for treatment of phimosis. The invention scope includes the pharmaceutical industry, prescription compounding services, and physicians.

Phimosis is more often suspected than actually found. What most frequently happens is an adhesion of the prepuce and the glans, which will detach normally from each other over time. Typically, the prepuce will not retract at birth, but this condition is often resolved within the initial four years of age. As the penis gets larger, epithelial debris will build up under the prepuce and eventually separate the prepuce from the glans. In countries where circumcision is not performed commonly, treatment is seldom found to be necessary. Spontaneous improvement comes with maturity.

The incidence of phimosis decreases from 8 percent to 1 percent in adolescents (Oster J, *Further Fate of the Foreskin*, Arch Dis Child, 1968, 43: 200-3). The number of cases is as low as 0.4/1000 boys per year.

In the last few years there has been a heated debate over routine circumcision Effective as it may be, this procedure may result in bleeding, meatal stenosis and tissue injuries which in turn may lead to an amputated glans or urethral coetaneous fistulas. In 1981 the circumcision rate was 80 percent in the USA. This rate has been diminishing over the last decades.

Phimosis is a vague term used commonly, and it generally means a condition in which the penis skin cannot be retracted. Rickwood described as true phimosis the presence of a whitish sclerotic ring keeping the prepuce from retracting. Studies conducted in the United Kingdom show that physicians are not trained to distinguish the normal development of preputial adhesions from pathologic phimosis. This indicates that normal development is improperly classified as phimosis. As a result, a large number of unnecessary circumcisions is performed.

The state of the art quotes the article *Phimosis: Is Circumcision Necessary* by Dewan P A, Tiv H C, Chieng B S, Journal of Paediatrics & Child Health, vol 32(4) August 1996 pp 284-289, which comments on the effectiveness of certain treatments that avoided circumcision surgery.

An article published on the British Journal of Urology: *The Conservative Treatment of Phimosis in Boys* by Golubovic Z, Milanovic D et al, vol 78(5), November 1996, pp 786-788, quotes a successful treatment in boys over three years of age who used 0.05 percent betamethasone cream topically as compared to patients that underwent a topical treatment using neutral cream petroleum jelly) only. The article *The treatment of Childhood Phimosis with Topical Steroid* by Pless T K, Spjeldness N, Jorgensen T M Ugeskrift for Laeger (DK), vol 161 (47), pp 6493-6495, 1999, describes the same type of treatment, i.e., topical application of 0.05 percent betamethasone cream.

Another article also describes infant treatment using topical application of 0.05 percent betamethasone cream: *Conservative Treatment of Phimosis in Children Using a Topic Steroid* by Orsola A, Caffaratti J, Garat J M, Urology (On-line), 56 (2): 307-10, Aug. 1, 2000.

Yet another article, *Topical Steroid Treatment of Phimosis in Boys*, by Chu C C, Chen K C, Diau G Y, The Journal of Urology, vol 162 (3-1) September 1999, pp 861-863, also comments on the results from topical application following hygienizing using 0.06 percent betamethasone cream. The article *Medical Management of Phimosis in Children: Our Experience with Topical Steroids* by Monsour M A, Rabinovitch H H, Dean G E, The Journal of Urology, vol 162 (3-II) September 1999, pp 1162-1164, comments on the successful topical treatment of boys with phimosis symptoms using 0.05 percent betamethasone cream.

For topical phimosis treatment there is a number of types of steroids, in the form of 0.5 percent betamethasone creams, 1 and 2 percent hydrocortisone, and 0.05 percent betamethasone, 0.05 percent clobetasol, corticoid together with HCG injection, 0.05 percent betamethasone, 0.1 percent strogen; 1 percent hydrocortisone, etc.

Wright reported a significant improvement in 80 percent of 111 patients treated with betamethasone cream (Wright J E, *The treatment of Childhood Phimosis with Topical Steroid*. Aust New Zeal J Surg, 1994, 64: 327-330). Lindhagen reported a 70 percent success using clobetasol propionate, a powerful corticosteroid, but this should be used with caution in these cases (Lindhagen T, *Topical Clobetasol Propionate Compared with Placebo in the Treatment of Unrectractable Foreskin*, Eur J Surg, 1996, 162:969-972). Kirikos et al (Kirikos C S; Beasley S W and Wood A A, *The Response of Phimosis to Local Steroid Application*, Pediatric Surgery, 1993, 8:329-332), showed improvement in around 80 percent using 2 percent hydrocortisone. There are no reports of local or systemic adverse effects (the corticoid absorption surface is as small as 0.1 percent of the body). These studies involved groups of patients with median of age around 6 years (2-15 years).

A conservative treatment is less costly than a surgical one. The betamethasone cream for 4 weeks was found effective, with a success rate of 70-75 percent less costly than circumcision (Van-Howe R S, *Cost-Effective Treatment of Phimosis*. Pediatrics, 1998, 102 (4):E43).

A controlled study (Atilla K K, Dündaroz R; Odabas Ö; Öztirk H; Akin R and Gökçay, *A Nonsurgical Approach to the Treatment of Phimosis: Local Nonsteroidal Anti-Inflammatory Ointment Application*, J. Urology, 1997, 158:196-197) used a non-steroidal anti-inflammatory agent instead of a corticoid as an alternative for cases in which corticosteroids are contraindicated. Around 75 percent of results—complete or partial improvement—were achieved.

Recent studies have described a more conservative approach to phimosis using both topical steroids and non-steroidal anti-inflammatory agents applied to the fibrotic ring. These reports have shown satisfactory results of 67-95 percent, with no adverse effects (Marzaro M, Carmignola G, Zoppellaro F, Schiavon G, Ferro M, Fusaro F, Bastasin F, Perrino G, Fimosi: *quando and patologia di interesse chirurgico?* Minerva Pediatr, 1997, 49(6):245-248).

None of these articles comments on the association of steroids with diffusing agents to render a treatment more effective.

In order to help fight the morbidity from circumcision, hemorrhage (4-6 percent), ulcer, and meatal stenosis (11 percent), infection (4-6 percent), urethral fistula, removal of improper amounts of skin resulting in a new phimosis, the Applicant developed a new treatment using topical corticosteroid application in association with diffusing enzyme, which proved a new effective treatment. A synergism was found to exist between the properties of proteolytic enzymes and corticosteroids in the treatment of phimosis, with more promising results than those obtained from the use of steroids, or corticosteroids where such enzymes are not present, such as symptoms disappearing within shorter periods of time.

The invention is intended to develop a new composition for topical treatment of phimosis to help the prepuce detach from the glans by impacting the depolymerization of the hyaluronic acid of the conjunctive tissue between both structures, so that a reduction can be achieved in the resolution time, side effects, effectiveness, and total treatment costs by using corticosteroids either or not associated with hormonal steroids, or non-steroidal anti-inflammatory agents and proteolytic diffusing enzymes.

This invention resulted in resolved phimosis in 90 percent of the patients between 1 and 30 years of age. Therefore, a patient—who in most cases is a child—is not exposed to the surgical trauma/risk. The prepuce skin remains integral, and the sensory and psychological functions are preserved.

This new topical application using composition for topical application using corticosteroids and/or hormone steroids in association with proteolytic diffusing enzyme, whether or not in the presence of non-hormonal anti-inflammatory agents, for treatment of phimosis, helps the prepuce detach from the glans by impacting the depolymerization of the hyaluronic acid of the conjunctive tissue between both structures, thus yielding unusual results.

This invention resulted in phimosis resolution in 90 percent of the patients aged 1 to 30 years. Therefore, patients—mostly children—are not exposed to the surgical trauma/risk. The prepuce skin remains integral, and the sensory and psychological functions are preserved.

This new invention is aimed at the treatment of phimosis in both children and adults using topical corticosteroid application in association with diffusing enzyme to prevent circumcision (surgical treatment), with better (90 percent) results in relation to the topical use of either steroidal or non-steroidal anti-inflammatory agents.

The association with the enzyme helps the prepuce detach from the glans by impacting the depolymerization of the hyaluronic acid of the conjunctive tissue between both structures, thus accentuating the local anesthetic and leading to the lysis of the adhesions between the prepuce and the glans, with better results than those obtained with the existing treatment of phimosis.

In conclusion, the association of corticosteroid with diffusing enzyme has proved more effective than all existing treatments and is an innovative therapy for both adult patients and pediatric ones.

The Applicant developed a pharmaceutical composition for treatment of phimosis using topical corticosteroid characterized by including around 0.025 to 5 percent in weight in relation to the total weight of the mixture composition of one or more corticosteroids and/or hormone steroids, whether or not associated with non-hormonal anti-inflammatory agents, and around 25 UI to 4000 UI/g of one or more proteolytic diffusing enzymes in proper medium, under different pharmaceutical forms, accompanied with additives known to the technical man.

Usable corticoids may be chosen from, for example, the group: Betamethasone, hydrocortisone, cortisone, hydrocortisone acetate or buteprate or butyrate or valerate, clobetasol or clobetasol propionate, propionate or dipropionate or valerate or phosphate or acetate and other esters of betamethasone, alclometasone dipropionate, deoxymetasone, clocortolone pivalate, diflorasone diacetate, fluocinolone acetonide, flurandrenolide, metilprednisolone acetate, mometasone furoate, diflorasone diacetate, amcinonide, fluocinonide, halobetazole propionate, desonide, triamcinolone acetonide and mixtures thereof, etc.

Ideally, around 0.5 to 3 percent in weight should be used in relation to the total weight of the mixture of one or more corticosteroids such as those of the betamethasone family, or 2-phenyl-1,2-benzisoselenasol-3(2H)-one and its by-products.

Betamethasone is a synthetic fluorinated corticosteroid in the form of a white or almost white crystalline powder, water-insoluble, and partially alcohol-soluble. It is used for this type of application, ideally in the form of ester such as valerate, propionate, dipropionate, phosphate, or acetate.

Hormonal steroids may be used in association with the composition's components such as testosterone.

Figure 1 shows the structural formula of betamethasone in its particularly usable form: Betamethasone valerate.

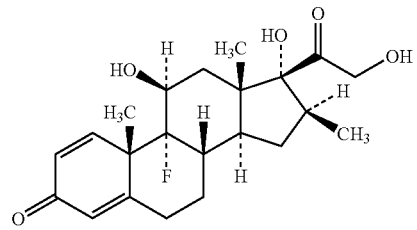

FIGURE 1

The steroidal agent may be alternatively used associated with one or more non-hormonal anti-inflammatory agents such as those chosen from the group: Diclofenac, ibuprofen, naproxen, fenoprofen, tolmetin, sulindac, meclofenamate, ketoprofen, piroxicam, flurbiprofet, oxaprozin, etc. Ideally, diclofenac is used.

Associated with those, one or more proteolytic diffusing enzymes of about 25 to 4000 UI/g are used, ideally within around 75 to 2000 UI/g such as hyaluronidase.

Hyaluronidase is prepared commercially using bovine or ovine testicles, or biotechnological processes, and is marketed in the form of sterile or nonsterile yophil.

Hyaluronidase depolymerizes the hyaluronic acid present in the interstitial substances of tissues, particularly the skin and synovial fluid. The hyaluronic acid consists of a chain of glycuronic-N-acetylglycosamine units polymerized by stable glycoside links, which are split by hyaluronidase. The resulting decreased viscosity
contributes to diffusing the substances through the tissues.

Hyaluronidase may be added to parenteral fluids such as saliva, glucose, lactate, and plasma to accelerate absorption and reduce local tissue distension. The absorption in traumatic edema or post-surgical regions, or hematoma may be accelerated by infiltration of hyaluronidase and use of a garrote. Likewise, the inflammation caused by accidental spilling of irritative solutions may be diminished.

The composition may be applied using gel, ointment, cream, aerosol, or any other form of topical application.

A few examples to illustrate the invention follow.

EXAMPLE 1

A prospective study was conducted with 100 male patients with phimosis diagnosis. Thirty-nine patients were between 1 and 5 years (3.25 years average)—group 1, and 61 between 6 and 30 years (12.49 years average)—group 2. No case referred topical or surgical treatment background, nor local inflammatory process. All patients were treated with topical compound made of 0.2 percent betamethasone added with 150 UI hyaluronidase prepared in the form of ointment. The patients were directed to use the ointment once or twice a day until process resolution, but not longer than 12 weeks.

The product was applied by the patient, or the parents if infants, to the fibrotic ring, then the prepuce was retracted slightly. Caution was taken to prevent the retraction from causing the patient pain or bleeding.

The treatment was found effective in the cases of complete phimosis resolution following the aforementioned period.

The patients were asked about the presence of local irritative symptoms, terminal dysuria, or bleeding during the treatment.

For analysis of the results both groups were compared for a possible relation between the patient's-age and the result from the medication and the time taken to obtain clinical improvement. For this the Student's T-Test was used to compare mean values, using a 5 percent level of significance.

Results

Ninety (90 percent) patients who reacted to the clinical treatment had phimosis resolution, and 32 percent had major prepuce retraction with no pain or bleeding, and 58 percent had complete symptomatology resolution.

Local irritative symptoms such as hyperemia and feeling of local burning were found in 5 percent of the patients, but those regressed completely after the treatment was suspended. After a few days with no application of the ointment the patients began to use it again with satisfactory results.

Five (5 percent) of the patients needed to be retreated, with satisfactory results.

The mean time of medication usage was 38 days for the group between 1 and 5 years and 42 days for the group between 6 and 30 years.

The statistical analysis did not show any differences between the clinical response and the time of usage of the compound between both groups, yielding statistically similar results between the age ranges evaluated ($p>0.05$).

EXAMPLE 2

A topical cream was prepared including:

| Betamethasone | 0.2 percent (in weight in relation to mass . . . ) |
| Hyaluronidase | 150 UI |
| Ointment | 1 g |

The procedure here was similar to that of the previous example for three patients with phimosis symptoms, as follows:

Patient 1

Patient 18 months of age with phimosis diagnosis, treated earlier with 0.05 percent hydrocortisone ointment with no results. The treatment began with the aforementioned association applied twice a day for four weeks with complete symptomatology resolution.

Patient 2

Patient 16 years of age, pubescent, and presenting phimosis.

The same treatment was administered for 8 weeks, with appropriate resolution at the sixth week. This is an evidence of its utility at higher age ranges.

Patient 3

Patient 7 years of age with phimosis recurrence following glans exposure with massages as instructed by a pediatrician.

The treatment began with the instruction that for secondary phimosis it could take as long as 12 weeks.

The treatment was effective after 10 weeks using the ointment.

| Patient | Age | Cream Comp sition | Application | Res luti n |
|---|---|---|---|---|
| 1 | 18 months | 0.2 percent betamethasone and 150 UI of hyaluronidase | twice a day for 4 weeks | Complete |
| 2 | 16 years | 0.2 percent betamethasone and 150 UI of hyaluronidase | twice a day for 8 weeks | Appropriate |
| 3 | 7 years | 0.2 percent betamethasone and 150 UI of hyaluronidase | secondary phimosis, twice a day for 10 weeks | Effective |

These are clinical examples in different situations of good clinical results that may be achieved using the mentioned ointment to prevent both the surgical trauma and additional costs.

The invention claimed is:

1. A pharmaceutical composition for treatment of phimosis comprising:
   0.025 to 5 percent in mixture of one or more corticosteroids of the betamethasone family, 25 UI/g to 4000 UI/g of one or more diffusing enzymes of the hyaluronidase family in medium, and additives;
   wherein the composition is in a form adapted to be applied topically; and wherein the form is chosen from an ointment, a gel, a cream, and a pomade.

2. A composition for treatment of phimosis according to claim 1 wherein said pharmaceutical composition comprises 0.5 to 3 percent by weight of the one or more corticosteroids in relation to the total weight of the composition.

3. A composition for treatment of phimosis according to claim 1 wherein said one or more corticosteroids of the betamethasone family is selected from betamethasone, hydrocortisone, hydrocortisone acetate, buteprate, butyrate, or valerate, clobetasol or clobetasol propionate, dipropionate, valerate, phosphate, acetate, or other esters of betamethasone, alclometasone dipropionate, deoxymetasone, clocortolone pivalate, diflorasone diacetate, fluocinolone acetonide, flurandrenolide, metilprednisolone acetate, mometazone furoate, diflorasone diacetate, amcinonide, fluocinonide, halobetazole propionate, desonide, triamcinolone acetonide and mixtures thereof.

4. A composition for treatment of phimosis according to claim 1 wherein said pharmaceutical composition comprises 75 to 2000 UI/g of one or more diffusing enzymes of the hyaluronidase family.

5. A composition for treatment of phimosis according to claim 3 wherein said one or more corticosteroids of the betamethasone family includes an ester, and wherein said ester is propionate, dipropionate, valerate, phosphate or acetate.

6. A composition for treatment of phimosis according to claim 1 further comprising at least one anti-inflammatory agent, wherein said at least one anti-inflammatory agent is chosen from Diclofenac, ibuprofen, naproxen, fenoprofen, tolmetin, sulindac, meclofenamate, ketoprofen, piroxicam, flurbiprofen, and oxaprozin.

7. A composition for treatment of phimosis according to claim 1 further comprising at least one hormonal steroid in association with said one or more corticosteroids.

8. A composition for treatment of phimosis according to claim 2 wherein said one or more corticosteroids of the betamethasone family is selected from betamethasone, hydrocortisone, hydrocortisone acetate, buteprate, butyrate, or valerate, clobetasol or clobetasol propionate, dipropionate, valerate, phosphate, acetate, or other esters of betamethasone, alclometasone dipropionate, deoxymetasone, clocortolone pivalate, diflorasone diacetate, fluocinolone acetonide, flurandrenolide, metilprednisolone acetate, mometazone furoate, diflorasone diacetate, amcinonide, fluocinonide, halobetazole propionate, desonide, triamcinolone acetonide and mixtures thereof.

\* \* \* \* \*

UNITED STATES PATENT AND TRADEMARK OFFICE
CERTIFICATE OF CORRECTION

PATENT NO. : 7,666,858 B2 Page 1 of 1
APPLICATION NO. : 10/465977
DATED : February 23, 2010
INVENTOR(S) : Paulo Cesar Rodriguez Palma It is certified that error appears in the above-identified patent and that said Letters Patent is hereby corrected as shown below:

Title page, Item [56], Column 2,
Lines 13-15, "A. Lamprakopoulos... Jul. 5, 2000." should be deleted, as it is a duplicate.

Column 1,
Line 59, "...neutral cream petroleum jelly) only." should be -- ...neutral cream (petroleum jelly) only. --.

Column 4,
Line 48, "...decreased viscosity" should be -- ...decreased viscosity contributes to diffusing the substances through the tissues. --. There should be no extra spacing between "viscosity" and "contributes".

Signed and Sealed this

Thirty-first Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,666,858 B2  
APPLICATION NO. : 10/465977  
DATED : February 23, 2010  
INVENTOR(S) : Paulo César Rodrigues Palma Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 824 days.

Signed and Sealed this

Twenty-eighth Day of December, 2010

David J. Kappos
*Director of the United States Patent and Trademark Office*